(12) United States Patent
Landegren

(10) Patent No.: US 6,878,515 B1
(45) Date of Patent: Apr. 12, 2005

(54) ULTRASENSITIVE IMMUNOASSAYS

(76) Inventor: Ulf Landegren, Eksoppsvägen 16, S-756 46 Uppsala (SE)

(*) Notice: Subject to any disclaimer, the term of this patent is extended or adjusted under 35 U.S.C. 154(b) by 212 days.

(21) Appl. No.: 08/981,310

(22) PCT Filed: Jun. 14, 1996

(86) PCT No.: PCT/SE96/00779

§ 371 (c)(1),
(2), (4) Date: Dec. 16, 1997

(87) PCT Pub. No.: WO97/00446

PCT Pub. Date: Jan. 3, 1997

(30) Foreign Application Priority Data

Jun. 16, 1995 (SE) ............................................. 9502196

(51) Int. Cl.[7] ............................................. C12Q 1/68
(52) U.S. Cl. ........................... 435/6; 435/7.1; 435/91.1; 435/91.2; 435/7.92; 435/7.94; 435/7.93; 435/975; 435/810; 436/518; 436/501; 514/44; 530/350; 530/387.1; 530/388.1
(58) Field of Search ........................... 435/6, 7.1, 91.1, 435/91.2, 7.94, 7.92, 7.93, 975, 810, 5, 7.9; 436/518, 501, 531; 514/44; 530/350, 387.1, 388.1

(56) References Cited

U.S. PATENT DOCUMENTS

| | | | | |
|---|---|---|---|---|
| 4,563,417 A | * | 1/1986 | Albarella et al. | 435/6 |
| 4,690,890 A | * | 9/1987 | Loor et al. | 435/7 |
| 4,748,111 A | * | 5/1988 | Dattagupta et al. | 435/6 |
| 4,824,775 A | * | 4/1989 | Dattagupta | 435/4 |
| 4,988,617 A | * | 1/1991 | Landegren et al. | 435/6 |
| 5,011,771 A | * | 4/1991 | Bellet et al. | 435/7.94 |
| 5,026,653 A | * | 6/1991 | Lee et al. | 436/518 |
| 5,079,172 A | * | 1/1992 | Hari et al. | 436/518 |
| 5,384,255 A | * | 1/1995 | Ciechanover et al. | 435/193 |
| 5,415,839 A | * | 5/1995 | Zaun et al. | 422/64 |
| 5,635,602 A | * | 6/1997 | Cantor | 530/391.1 |
| 5,656,731 A | * | 8/1997 | Urdea | 530/391.1 |
| 5,667,974 A | * | 9/1997 | Birkenmeyer et al. | 435/6 |
| 5,693,764 A | * | 12/1997 | Haley et al. | 530/391.1 |
| 5,759,773 A | | 6/1998 | Tyagi et al. | |
| 5,780,231 A | * | 7/1998 | Brenner | 435/6 |
| 5,804,384 A | * | 9/1998 | Muller et al. | 435/6 |
| 5,812,272 A | * | 9/1998 | King et al. | 356/445 |
| 5,814,492 A | * | 9/1998 | Carrino et al. | 435/91.2 |
| 5,830,670 A | * | 11/1998 | De La Monte et al. | 435/7.2 |
| 5,849,878 A | * | 12/1998 | Cantor et al. | 530/391 |
| 5,876,976 A | * | 3/1999 | Richards et al. | 435/91.2 |
| 5,919,626 A | * | 7/1999 | Shi et al. | 435/6 |
| 5,962,223 A | * | 10/1999 | Whiteley | 435/6 |
| 6,143,508 A | * | 11/2000 | Okarma | 435/7.21 |
| 6,511,809 B2 | | 1/2003 | Baez et al. | |

FOREIGN PATENT DOCUMENTS

| | | | |
|---|---|---|---|
| WO | WO9117442 A1 | | 11/1991 |
| WO | 9320227 | * | 10/1993 |
| WO | 9416105 | * | 7/1994 |

OTHER PUBLICATIONS

US 5,219,734, 6/1993, Royer et al. (withdrawn)
Suzuki, A et al, Japanese Journal of Cancer Research, vol. 86(9), Sep. 1995, pp. 885–889, Double determinant immuno–polymerase chain reaction, a sensitive method for detecting circulating antigens in human sera.*

(Continued)

Primary Examiner—Lynette R. F. Smith
Assistant Examiner—Ginny Allen Portner
(74) Attorney, Agent, or Firm—Birch, Stewart, Kolasch & Birch, LLP

(57) ABSTRACT

The present invention relates to an immunological test kit and immunoassay using a first immobilized antibody having affinity for a specific antigen. The invention is characterized by a second and third antibody being specific for different determinants of the antigen and modified with cross-linkable oligonucleotides. For detection, the oligonucleotides are amplified, whereby only such oligonucleotides will be amplified which have been cross-linked to each other. In this way unspecific background is avoided and detection is possible down to single molecules.

8 Claims, 1 Drawing Sheet

OTHER PUBLICATIONS

Figure 1:
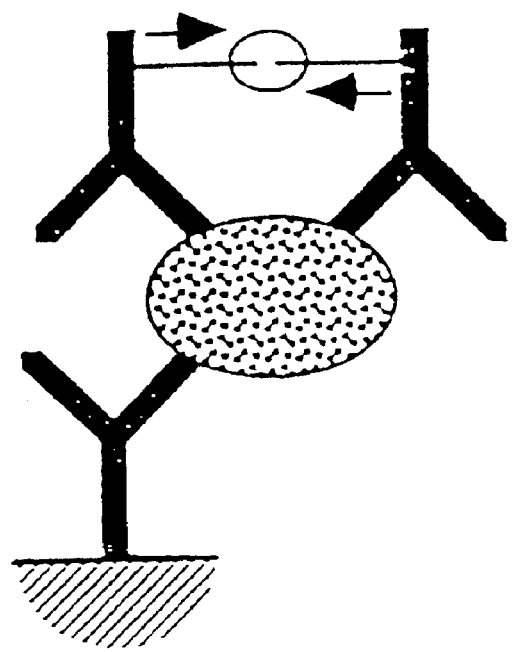

Nickerson et al (1992),Genomics, vol. 12(2), pp. 377–387.*
Delahunty et al (1995), Clin. Chem.,vol. 41(1), 59–61.*
Kwok et al (1992)Genomics, vol. 13(4), pp. 935–941.*
Nilsson et al (1994)Science, vol. 265(518), pp. 2085–2088.*
Hendrickson et al, Nucleic Acid Research, vol. 23(3), pp. 522–529, 1995.*
Barany, F., PCR Methods and Applications, Aug., vol. 1(1), pp. 5–16, 1991.*
Barany, F., Proc. Natl. Acad. Sci, USA vol. 88, pp. 189–193, Jan., 1991.*
Wiedmann et al, PCR Methods and Applications, Cold Spring Harbor Laboratory, pp. S51–S64, 1994.*
T. Sano, et al., Chemtech, 24: 24–29 (1995).
Nickerson et al, 1992, Genomics, vol. 12(2), p377–387.*
Delahunty, C.M et al, 1995, Clin. Chem., vol. 41(1), p59–61.*
Kwok, P–Y et al, 1992, Genomics, vol. 13(4), p 935–941.*
Nilsson et al, 1994, Science, vol. 265(5181), p2085–p 2088.*
Delahunty, C. et al, Am. J. Human Genetics, vol. 58(6) 1996, p 1239–1246.*
Langerstrom, M. et al, PCR Methods Appl., Nov. 1991, vol. 1(2), p111–119.*
Landegren, U., Bioessays, vol. 15(11), 1993, p 761–765.*
Landegren, U.; Genet Anal. Tech. Appl., vol. 9(1), 1992, p 3–8.*
Nickerson, D.A et al, Proc. Natl. Acad. Sci (USA), vol. 87, Nov. 1990, p 8923–8927.*
Samiotaki, M. et al, Genomics, vol. 20(2), 1994, p 238–242.*
Samiotaki, M. et al, Am. J. Human Genet., vol. 43, (4 suppl.), 1991, p. 194.*
Tobe, V.O. et al, Nucleic Acid Res., vol. 24(19), 1996, p 3728–3732.*
Hendrickson et al., *Nucleic Acids Research,* vol. 23, No. 3, pp. 522–529 (1995).
Sano et al., *Science,* vol. 258, pp. 120–122 (Oct. 1992).

* cited by examiner

ULTRASENSITIVE IMMUNOASSAYS

This application is the national phase under 35 U.S.C. §371 of prior PCT International Application No. PCT/SE 96/00779 which has an International filing date of Jun. 14, 1996 which designated the United States of America, the entire contents of which are hereby incorporated by reference.

Technical field

The present invention relates to ultrasensitive immunoassays. More specifically, it relates to immunological test kits and processes for immunological detection of a specific antigen. In the present invention, the fields of immunology and molecular genetics are combined.

BACKGROUND OF THE INVENTION

Immunoassays represent powerful tools to identify a very wide range of compounds, such as antigens and antibodies. Examples of immunoassays are ELISA (enzyme linked immunosorbent assay), EIA (enzyme immunoassay), and RIA (radio immunoassay). Common to all these immunoassays, is that detection sensitivity is limited by the affinity of typical antibodies.

With the prior art immunoassays, detection is not possible below a certain number of molecules, because the background, i.e. unspecifically bound material, interferes with the results. Detection of very low numbers of antigen is becoming increasingly important, especially for diagnostic applications. Therefore, further developments in sensitivity as well as specificity of immunological assays are desired.

Cantor et al, Science, Vol. 258, 2 October 1992, have previously reported the attachment of oligonucleotides to antibodies in order to permit detection of such antibodies having bound antigen in immune reactions. A streptavidin-protein A chimera that posseses tight and specific binding affinity for both biotin and immunoglobulin G was used to attach biotinylated DNA specifically to antigen-monoclonal antibody complexes that had been immobilized on microtiter plate wells. Then, a segment of the attached DNA was amplified by PCR (Polymerase Chain Reaction). Analysis of the PCR products by agarose gel electrophoresis after staining with ethidium bromide allowed detection of 580 antigen molecules ($9.6 \times 10^{-22}$ moles) which is a significant improvement compared to, for example, conventional ELISA.

However, in Cantor et al., the labeled DNA-antibody complexes are assembled in situ during the assay. This can create variable stoichiometry in the assembly of the components and in the attachment of the DNA label. Moreover, extra steps are required for addition of biotinylated reagents and binding proteins. Numerous wash steps are also needed to remove excess reagents and to free assay components of non-specifically bound reagents.

Hendrickson et al., Nucleic Acids Research, 1995, Vol 23, No.3, report an advancement of the Cantor et al. assay that reduces complexity. This is achieved through labeling antibody with DNA by direct covalent linkage of the DNA to the antibody. In this approach, the analyte specific antibody and the 5' amino modified DNA oligonucleotide are independently activated by means of separate heterobifunctional cross-linking agents. The activated antibody and DNA label are then coupled in a single spontaneous reaction.

International patent publication no. WO 91/17442 describes a molecular probe for use as a signal amplifier in immunoassays for detecting i.a. antigens. The probe comprises an antibody, a double stranded polynucleotide functioning as a promoter for a DNA dependend RNA polymerase, and a single or double stranded template for the promoter. The transcription product is quantified and correlated to the amount of present antigen in a sample.

However, in all three of the above described immunoassays the attached DNA is only used as a marker by being amplified to detectable levels. There is no distinction between oligonucleotides attached to antibodies having bound antigen and oligonucleotides attached to antibodies not having bound antigen, i.e. those being non-specifically trapped. Non-specifically trapped antibodies give rise to an undesired background signal and limits the minimun number of antigen molecules that can be detected and it will not be possible to distinguish between false positive and true positive results below a certain number of antigen molecules. Commonly, solid supports such as microtiter plates, are used for the reactions. According to prior art, there will always be an excess of oligonucleotide-labeled antibody that cannot be removed from the solid support by adding background-lowering agents and by repeated wash steps.

SUMMARY OF THE INVENTION

The present invention enables detection of extremely low numbers of antigenic molecules, even down to a single molecule. The invention provides reliable immunoassays in situations where insufficient numbers of antigens are available for conventional assays.

According to a first aspect of the invention, there is provided an immunological test kit comprising a first immobilized reagent having affinity for a specific macromolecule, such as a protein. Furthermore, the test kit comprises a second and a third affinity reagent specific for different determinantes of said macromolecule, and modified with crosslinkable compounds enabling a) conjugation of said second and third affinity reagent only when both are bound to the said, same macromolecule, and b) detection by amplification.

According to a preferred embodiment of the invention, the affinity reagents are antibodies and the crosslinkable compounds are oligonucleotide extensions attached to the second and third antibody, respectively. The macromolecule is in this case a specific antigen.

According to a second aspect of the invention there is provided an immunoassay for detection of a specific antigen, comprising the following steps:

a) contacting a sample suspected of containing said specific antigen with a first antibody linked to a solid support, said first antibody being specific for a first epitope on the antigen, b) washing off excess reagents, c) incubating with a solution of a second and a third antibody specific for a second and third epitope of said antigen, and modified with crosslinkable oligonucleotides enabling conjugation of said second and third antibody when both are bound to the said, same antigen, d) washing off excess reagents, e) amplifying said crosslinked oligonucleotides, and f) detecting the amplified products.

Products from the amplification reaction only result when two antibodies, i.e. the second and the third, have bound to the same antigen. Thus, amplification is specific for antibodies having bound to antigen. Non-specifically trapped antibodies do not give rise to any signal.

DETAILED DESCRIPTION OF THE INVENTION

Figure 2:
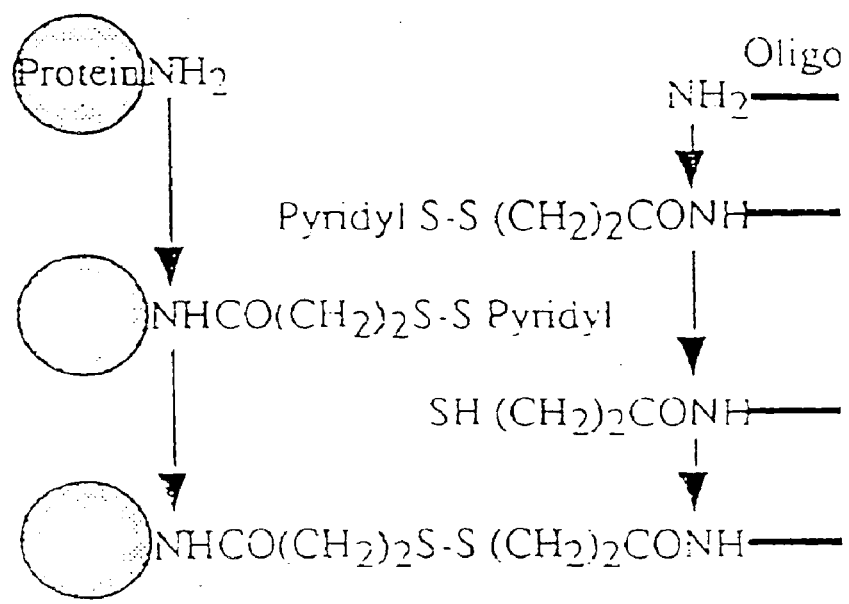

The present invention will be described more detailed below with reference to the accompanying drawings, in which FIG. 1 is a schematic view of the principles of the immunoassay according to the invention, and FIG. 2 shows chemical coupling of amino-modified oligonucleotides to macromolecules.

In FIG. 1 there is shown an immobilized antibody to a specific antigen applied together with two other antibodies, specific for other determinants on the same antigen. Besides antibodies other specifically interacting species with a known affinity, such as lectins, receptors, single chain antibodies, cofactors, oligonucleotides and other non-proteins, can be used in the invention.

The interacting species are modified with crosslinkable compounds in the form of an interacting pair, preferably short oligonucleotide extensions. Upon the coordinated binding of several so modified antibodies, oligonucleotides of neighbouring antibodies are conjugated to each other. The conjugation may or may not necessitate an enzymatic ligation step depending on the orientation of the oligonucleotide extensions.

If the conjugation is between free 3' and 5' ends ligation is necessary, such as by T4 RNA ligase or T4 DNA ligase. To facilitate the conjugation, it is convenient to use a stretch of oligonucleotides base pairing to and, thereby, juxtaposing the free ends of the oligonucleotides and permitting their joining through ligation.

If the conjugation is between free 3' ends these have to be designed to be mutually complementary to achieve base pairing and initiation of DNA synthesis extending the 3' ends of the the molecules.

Thus, only in those cases where the antibodies are brought close enough through binding to the same antigen molecule can the oligonucleotides be ligated. Ligated molecules subsequently serve as templates for nucleic acid amplification reactions.

In FIG. 2, there is shown a suitable way to attach the oligonucleotide extension to the antibodies. First, the oligonucleotides are terminally amino-modified and then attached to primary amines on the antibodies via disulphide bonds, e.g. according to the technique of Chue and Orgel, Nucleic Acid Research, Vol. 16, No. 9, 1988. Another way is by direct covalent coupling as described by Hendrickson et el., supra.

The antibodies used in the invention can be polyclonal, monoclonal or single chain antibodies produced by bacteriophages. In the latter case, it is possible to have antibodies equipped with an oligonucleotide binding part, rendering the above coupling step between antibody and oligonucleotide unnecessary.

The amplification technique to obtain detectable products is, for example, PCR (Polymerase Chain Reaction), LCR (Ligase Chain Reaction), SDA (Strand Displacement Amplification) bacteriophage Qβ replication, and 3SR (Self-Sustained Synthetic Reaction), of which the latter three methods do not require temperature cycling.

The method for detecting amplified products can, for example, be direct incorporation of a label, such as radioisotopes, fluorochromes, and enzymes, into the amplified products with the use of label-conjugated primers or nucleotides. Preferably, the accumulation of amplified products is monitored via the fluorescence from intercalating dyes, such as propidium iodide, etidium bromide and SYBR™ green from Molecular Probes.

The invention is not restricted to detection of any special kind of macromolecule, such as an antigen; the only criterion it has to fulfil is that it must be able to simultaneously bind three antibodies/affinity reagents. In the case where the affinity reagents are antibodies, the three antibodies are specific for different epitopes on the antigen. By biosensor analysis, it is possible to assure that the antibodies do not bind to overlapping epitopes on the antigen.

Examples of macromolecules are human myoglobin and human growth hormone. Ultrasensitive assays for growth hormone will have significant value in clinical situations where hormone levels are undetectable by prior art assays.

The invention will now be described below in a non-limiting example.

EXAMPLE

Immunoglobulins were modified in a reaction with SPDP (3-(-pyridyldithio) propionic acid N-hydroxysuccinimide ester, from Pharmacia Biotech) according to the manufacturer's suggestions. Oligonucleotides were thiolated, either through the addition of a suitable phosphoramidite according to Connolly (Connolly BA, Nucl. Acid. Res. 1987 15:3131), or 3'aminomodified oligonucleotides were reacted with SPDP, followed by reduction of the dithiopyridyl bond, using dithiothreitol.

SPDP-modified antibodies were incubated with three equivalents of SH-containing oligonucleotides at 4° C. over night. The reaction mixture was separated using a Zorbax HPLC gel filtration column. Residual free antibody were removed from the isolated conjugate by ion exchange MonoQ FPLC separation.

The two oligonucleotides used to conjugate the antibodies were oligo 1: 5'Tr S C3-ATA GAC TGA GCG TGG ACA TTA ATA TGT ACG TAG GCT TTA TTG AGT 3' (SEQ ID NO:1) and Oligo 2: 5'P ATG TAC GAC CCG TAG ATA TTA TCA TAC TGG CAT GGG CAT GAT GAA CAT C-NHSPDP T3' (SEQ ID NO:2).

The immune test was performed by first binding 1pg of biotinylated antibody (#1) to individual streptavidin-coated prongs on a manifold support. [Parik et al., Anal. Biochem; (1993) 211: 144–150B]. After washes using PBS (phosfihate buffered saline) with 0.5% Tween 20, the prongs were lowered into solutions of antigen (myoglobin) at variable concentrations. After further washes, the supports with bound antigen were incubated in a solution of two oligonucleotide-conjugated antibodies #2 and #3 at 5 ng each per reaction. The supports were washed, an oligonucleotide complementary to the free ends of the antibody-conjugated oligonucleotides was added (4 pmol per reaction, 5'CTA CGG GTC GTA CAT ACT CAA TTA AGC GTA 3'(SEQ ID NO:3)), and the ends of oligonucleotides on nearby antibodies were joined covalently by ligation at 37° C. for 30 min using 1 U of T4 DNA ligase. The supports were then washed in a standard PCR buffer, and the supports were added as templates in a PCR mix, including two primers specific for sequences located at either side of the ligation junction (5'TTA ATG GCG AG 3' (SEQ ID NO:4)) and Taq polymerase. After two cycles, the supports were removed and the amplification was continued for 26 more cycles. Amplification products were examined by separation in an agarose gel and ethidium bromide staining.

What is claimed is:

1. A test kit comprising
   a) a first immobilized reagent having affinity to a specific macromolecule, and
   b) a second and a third affinity reagent specific for different determinants of said macromolecule, and modified with conjugatable oligonucleotides which conjugate through
      i) hybridization of an oligonucleotide complementary to the conjugatable oligonucleotides;
      ii) hybridization of the conjugatable oligonucleotides to each other; or
      iii) ligation of the oligonucleotides,
   wherein a signal is generated by nucleic acid amplification only when said second and third affinity reagents are closely bound on said macromolecule; wherein said macromolecule is a protein.

2. The test kit according to claim 1, wherein the affinity reagents are antibodies.

3. The test kit according to claim 1 or 2, wherein the oligonucleotides are complementary to each other.

4. The test kit according to claim 1, further comprising a ligase.

5. An immunoassay for detection of a specific antigen, comprising:
   a) contacting a sample suspected of containing said specific antigen with a first antibody linked to a solid support, said first antibody being specific for a first epitope on the antigen;
   b) washing off excess sample;
   c) incubating with a solution of a second and a third antibody specific for a second and a third epitope of said antigen, and modified with conjugatable oligonucleotides, wherein said oligonucleotides conjugate to each other when said second and third antibody are both bound to said antigen through i) hybridization of an oligonucleotide complementary to the conjugatable oligonucleotides;
ii) hybridization of the conjugatable oligonucleotides to each other; or
iii) ligation of the oligonucleotides;

d) washing off excess solution;
e) amplifying said conjugated oligonucleotides; and
f) detecting the amplified products.

6. An immunoassay according to claim 5, wherein the conjugation occurs through hybridization of an oligonucleotide complementary to the conjugatable oligonucleotides.

7. An immunoassay according to claim 5, wherein the conjugation occurs through hybridization of the conjugatable oligonucleotides to each other.

8. An immunoassay according to claim 6, wherein the conjugation occurs through ligation of the oligonucleotides.

* * * * *

SEQUENCE LISTING

<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 1
atagactgag cgtggacatt aatatgtacg tacgcttaat tgagt                45

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 2
atgtacgacc cgtagatatt atcatactgg catgggcatg gcatgaaca tc          52

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctacgggtcg tacatactca attaagcgta                                  30

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence:Synthetic
      primer

<400> SEQUENCE: 4
ttaatggcga g                                                      11